(12) United States Patent
Shah et al.

(10) Patent No.: US 8,160,683 B2
(45) Date of Patent: Apr. 17, 2012

(54) SYSTEM AND METHOD FOR INTEGRATING VOICE WITH A MEDICAL DEVICE

(75) Inventors: Jayesh Shah, Pleasanton, CA (US); Scott Amundson, Oakland, CA (US)

(73) Assignee: Nellcor Puritan Bennett LLC, Boulder, CO (US)

( * ) Notice: Subject to any disclaimer, the term of this patent is extended or adjusted under 35 U.S.C. 154(b) by 0 days.

(21) Appl. No.: 12/981,974

(22) Filed: Dec. 30, 2010

(65) Prior Publication Data

US 2011/0098544 A1 Apr. 28, 2011

Related U.S. Application Data

(63) Continuation of application No. 11/540,457, filed on Sep. 29, 2006, now abandoned.

(51) Int. Cl.
*A61B 5/00* (2006.01)

(52) U.S. Cl. ......... 600/509; 600/481; 600/300; 704/275

(58) Field of Classification Search .................. 600/300, 600/301, 513, 509, 508, 523, 483, 532; 128/903, 128/904, 920; 340/573.1, 539.11; 725/116; 705/3, 2; 700/242; 704/270, 275
See application file for complete search history.

(56) References Cited

U.S. PATENT DOCUMENTS

| | | | |
|---|---|---|---|
| 3,638,640 A | 2/1972 | Shaw | |
| 4,621,643 A | 11/1986 | New, Jr. et al. | |
| 4,653,498 A | 3/1987 | New, Jr. et al. | |
| 4,700,708 A | 10/1987 | New, Jr. et al. | |
| 4,714,341 A | 12/1987 | Hamaguri et al. | |
| 4,770,179 A | 9/1988 | New, Jr. et al. | |
| 4,805,623 A | 2/1989 | Jobsis | |
| 4,869,254 A | 9/1989 | Stone et al. | |
| 4,911,167 A | 3/1990 | Corenman et al. | |
| 4,936,679 A | 6/1990 | Mersch | |
| 4,972,331 A | 11/1990 | Chance | |
| 5,078,163 A | 1/1992 | Stone et al. | |
| 5,119,815 A | 6/1992 | Chance | |
| 5,122,974 A | 6/1992 | Chance | |
| 5,167,230 A | 12/1992 | Chance | |
| 5,267,174 A | 11/1993 | Kaufman et al. | |
| 5,297,548 A | 3/1994 | Pologe | |

(Continued)

FOREIGN PATENT DOCUMENTS

DE 10213692 A1 10/2003

(Continued)

OTHER PUBLICATIONS

Lee, Jason C.S., et al., "Measurement of Percent Carboxyhemoglobin with Pulse-Oximetry Technique," *IEEE Engineering in Medicine & Biology Society 10th Annual International Conference*, CH2566-88, vol. 88, pp. 1781-1782 (1988).

(Continued)

*Primary Examiner* — Vijay B Chawan (57) ABSTRACT

There is provided a system and method for integrating voice with a medical device. More specifically, in one embodiment, there is provided a medical device comprising a speech recognition system configured to receive a processed voice, compare the processed voice to a speech database, identify a command for the medical device corresponding to the processed voice based on the comparison, and execute the identified medical device command.

26 Claims, 7 Drawing Sheets

U.S. PATENT DOCUMENTS

| | | | |
|---|---|---|---|
| 5,329,459 A | 7/1994 | Kaufman et al. |
| 5,348,008 A | 9/1994 | Bornn et al. |
| 5,351,685 A | 10/1994 | Potratz |
| 5,355,880 A | 10/1994 | Thomas et al. |
| 5,368,026 A | 11/1994 | Swedlow et al. |
| 5,372,136 A | 12/1994 | Steuer et al. |
| 5,385,143 A | 1/1995 | Aoyagi |
| 5,482,036 A | 1/1996 | Diab et al. |
| 5,533,507 A | 7/1996 | Potratz |
| 5,553,614 A | 9/1996 | Chance |
| 5,564,417 A | 10/1996 | Chance |
| 5,572,241 A | 11/1996 | Kanayama et al. |
| 5,575,285 A | 11/1996 | Takanashi et al. |
| 5,594,638 A | 1/1997 | Illiff |
| 5,630,413 A | 5/1997 | Thomas et al. |
| 5,645,059 A | 7/1997 | Fein et al. |
| 5,645,060 A | 7/1997 | Yorkey |
| 5,662,106 A | 9/1997 | Swedlow et al. |
| 5,692,503 A | 12/1997 | Kuenstner |
| 5,754,111 A | 5/1998 | Garcia |
| 5,758,644 A | 6/1998 | Diab et al. |
| 5,779,631 A | 7/1998 | Chance |
| 5,806,515 A | 9/1998 | Bare et al. |
| 5,830,139 A | 11/1998 | Abreu |
| 5,842,981 A | 12/1998 | Larsen et al. |
| 5,873,821 A | 2/1999 | Chance et al. |
| 5,995,856 A | 11/1999 | Mannheimer et al. |
| 6,011,986 A | 1/2000 | Diab et al. |
| 6,035,223 A | 3/2000 | Baker |
| 6,064,898 A | 5/2000 | Aldrich |
| 6,120,460 A | 9/2000 | Abreu |
| 6,134,460 A | 10/2000 | Chance |
| 6,163,715 A | 12/2000 | Larsen et al. |
| 6,181,958 B1 | 1/2001 | Steuer et al. |
| 6,230,035 B1 | 5/2001 | Aoyagi et al. |
| 6,266,546 B1 | 7/2001 | Steuer et al. |
| 6,312,393 B1 | 11/2001 | Abreu |
| 6,397,091 B2 | 5/2002 | Diab et al. |
| 6,415,236 B2 | 7/2002 | Kobayashi et al. |
| 6,438,399 B1 | 8/2002 | Kurth |
| 6,445,597 B1 | 9/2002 | Boylan et al. |
| 6,478,800 B1 | 11/2002 | Fraser et al. |
| 6,487,439 B1 | 11/2002 | Skladnev et al. |
| 6,501,974 B2 | 12/2002 | Huiku |
| 6,501,975 B2 | 12/2002 | Diab et al. |
| 6,526,301 B2 | 2/2003 | Larsen et al. |
| 6,544,193 B2 | 4/2003 | Abreu |
| 6,546,267 B1 | 4/2003 | Sugiura et al. |
| 6,549,795 B1 | 4/2003 | Chance |
| 6,591,122 B2 | 7/2003 | Schmitt |
| 6,594,513 B1 | 7/2003 | Jobsis et al. |
| 6,606,509 B2 | 8/2003 | Schmitt |
| 6,615,064 B1 | 9/2003 | Aldrich |
| 6,622,095 B2 | 9/2003 | Kobayashi et al. |
| 6,658,277 B2 | 12/2003 | Wasserman |
| 6,662,030 B2 | 12/2003 | Khalil et al. |
| 6,671,526 B1 | 12/2003 | Aoyagi et al. |
| 6,671,528 B2 | 12/2003 | Steuer et al. |
| 6,678,543 B2 | 1/2004 | Diab et al. |
| 6,690,958 B1 | 2/2004 | Walker et al. |
| 6,693,812 B1 | 2/2004 | Li et al. |
| 6,708,048 B1 | 3/2004 | Chance |
| 6,711,424 B1 | 3/2004 | Fine et al. |
| 6,711,425 B1 | 3/2004 | Reuss |
| 6,748,254 B2 | 6/2004 | O'Neil et al. |
| 6,785,568 B2 | 8/2004 | Chance |
| 6,801,797 B2 | 10/2004 | Mannheimer et al. |
| 6,801,799 B2 | 10/2004 | Mendelson |
| 6,849,045 B2 | 2/2005 | Illiff |
| 6,873,865 B2 | 3/2005 | Steuer et al. |
| 6,934,571 B2 | 8/2005 | Wiesmann et al. |
| 6,947,780 B2 | 9/2005 | Scharf |
| 6,949,081 B1 | 9/2005 | Chance |
| 6,961,598 B2 | 11/2005 | Diab |
| 6,996,427 B2 | 2/2006 | Ali et al. |
| 7,001,334 B2 | 2/2006 | Reed et al. |
| 7,024,233 B2 | 4/2006 | Ali et al. |
| 7,027,849 B2 | 4/2006 | Al-Ali |
| 7,136,684 B2 | 11/2006 | Matsuura et al. |
| 7,186,966 B2 | 3/2007 | Al-Ali |
| 7,209,775 B2 | 4/2007 | Bae et al. |
| 7,306,560 B2 | 12/2007 | Illiff |
| 7,539,532 B2 | 5/2009 | Tran |
| 7,539,533 B2* | 5/2009 | Tran .......................... 600/509 |
| 7,698,002 B2 | 4/2010 | Music et al. |
| 7,706,896 B2 | 4/2010 | Music et al. |
| 2001/0005773 A1 | 6/2001 | Larsen et al. |
| 2001/0020122 A1 | 9/2001 | Steuer et al. |
| 2001/0039376 A1 | 11/2001 | Steuer et al. |
| 2001/0044700 A1 | 11/2001 | Kobayashi et al. |
| 2002/0026106 A1 | 2/2002 | Khalil et al. |
| 2002/0035318 A1 | 3/2002 | Mannheimer et al. |
| 2002/0038079 A1 | 3/2002 | Steuer et al. |
| 2002/0038081 A1 | 3/2002 | Fein et al. |
| 2002/0042558 A1 | 4/2002 | Mendelson |
| 2002/0049389 A1 | 4/2002 | Abreu |
| 2002/0062071 A1 | 5/2002 | Diab et al. |
| 2002/0111748 A1 | 8/2002 | Kobayashi et al. |
| 2002/0133068 A1 | 9/2002 | Huiku |
| 2002/0161287 A1 | 10/2002 | Schmitt |
| 2002/0161290 A1 | 10/2002 | Chance |
| 2002/0165439 A1 | 11/2002 | Schmitt |
| 2002/0173721 A1 | 11/2002 | Grunwald et al. |
| 2002/0198443 A1 | 12/2002 | Ting |
| 2003/0023140 A1 | 1/2003 | Chance |
| 2003/0055324 A1 | 3/2003 | Wasserman |
| 2003/0060693 A1 | 3/2003 | Monfre et al. |
| 2003/0093503 A1 | 5/2003 | Yamaki et al. |
| 2003/0130016 A1 | 7/2003 | Matsuura et al. |
| 2003/0135095 A1 | 7/2003 | Illiff |
| 2003/0139687 A1 | 7/2003 | Abreu |
| 2003/0144584 A1 | 7/2003 | Mendelson |
| 2003/0195402 A1 | 10/2003 | Fein et al. |
| 2003/0220548 A1 | 11/2003 | Schmitt |
| 2003/0220576 A1 | 11/2003 | Diab |
| 2004/0006261 A1 | 1/2004 | Swedlow et al. |
| 2004/0010188 A1 | 1/2004 | Wasserman |
| 2004/0054270 A1 | 3/2004 | Pewzner et al. |
| 2004/0087846 A1 | 5/2004 | Wasserman |
| 2004/0107065 A1 | 6/2004 | Al-Ali |
| 2004/0127779 A1 | 7/2004 | Steuer et al. |
| 2004/0162472 A1 | 8/2004 | Berson et al. |
| 2004/0171920 A1 | 9/2004 | Mannheimer et al. |
| 2004/0176670 A1 | 9/2004 | Takamura et al. |
| 2004/0176671 A1 | 9/2004 | Fine et al. |
| 2004/0204635 A1 | 10/2004 | Scharf et al. |
| 2004/0215958 A1 | 10/2004 | Ellis et al. |
| 2004/0230106 A1 | 11/2004 | Schmitt et al. |
| 2005/0033580 A1 | 2/2005 | Wang et al. |
| 2005/0080323 A1 | 4/2005 | Kato |
| 2005/0101850 A1 | 5/2005 | Parker |
| 2005/0107676 A1 | 5/2005 | Acosta et al. |
| 2005/0113656 A1 | 5/2005 | Chance |
| 2005/0168722 A1 | 8/2005 | Forstner et al. |
| 2005/0192488 A1 | 9/2005 | Bryenton et al. |
| 2005/0203357 A1 | 9/2005 | Debreczeny et al. |
| 2005/0267346 A1 | 12/2005 | Faber et al. |
| 2005/0280531 A1 | 12/2005 | Fadem et al. |
| 2006/0009688 A1 | 1/2006 | Lamego et al. |
| 2006/0015021 A1 | 1/2006 | Cheng |
| 2006/0020181 A1 | 1/2006 | Schmitt |
| 2006/0025660 A1 | 2/2006 | Swedlow et al. |
| 2006/0030762 A1 | 2/2006 | David et al. |
| 2006/0030763 A1 | 2/2006 | Mannheimer et al. |
| 2006/0030765 A1 | 2/2006 | Swedlow et al. |
| 2006/0052680 A1 | 3/2006 | Diab |
| 2006/0058683 A1 | 3/2006 | Chance |
| 2006/0058691 A1 | 3/2006 | Kiani |
| 2006/0142740 A1 | 6/2006 | Sherman et al. |
| 2006/0195025 A1 | 8/2006 | Ali et al. |
| 2006/0220881 A1 | 10/2006 | Al-Ali et al. |
| 2006/0226992 A1 | 10/2006 | Al-Ali et al. |
| 2006/0238358 A1 | 10/2006 | Al-Ali et al. |
| 2007/0265533 A1 | 11/2007 | Tran |
| 2007/0270665 A1 | 11/2007 | Yang et al. |
| 2008/0004904 A1 | 1/2008 | Tran |
| 2008/0082338 A1 | 4/2008 | O'Neil et al. |

| | | |
|---|---|---|
| 2008/0082339 A1 | 4/2008 | Li et al. |
| 2008/0097175 A1 | 4/2008 | Boyce et al. |
| 2008/0097176 A1 | 4/2008 | Music et al. |
| 2008/0097177 A1 | 4/2008 | Music et al. |
| 2008/0208009 A1 | 8/2008 | Shklarski |
| 2008/0242959 A1 | 10/2008 | Xu et al. |

FOREIGN PATENT DOCUMENTS

| | | |
|---|---|---|
| EP | 1905356 A1 | 4/2008 |
| EP | 1986543 A1 | 11/2008 |
| JP | 5212016 | 8/1993 |
| WO | WO9220273 | 11/1992 |
| WO | WO9403102 | 2/1994 |
| WO | WO9749330 | 12/1997 |
| WO | WO0145553 A1 | 6/2001 |
| WO | WO2006006158 A1 | 1/2006 |
| WO | WO2006009830 A2 | 1/2006 |
| WO | WO2006039752 A1 | 4/2006 |
| WO | WO2007017777 A2 | 2/2007 |
| WO | WO2007097754 A1 | 8/2007 |
| WO | WO2007140151A21 | 12/2007 |

OTHER PUBLICATIONS

Lee, Jason C.S., et al., "Simultaneous Measurement of Percent Carboxyhemoglobin and Functional Oxygen Saturation," *IEEE Engineering in Medicine and Biology Society*, CH2770-6, vol. 89, pp. 1092-1093, 1989.

Bongard, Frederic S., et al., "Continuous Dual Oximetry in Surgical critical care—Indications and Limitations," *Annals of Surgery*, vol. 216, No. 1, pp. 60-68 (1992).

Sherman, Bruce, MD. et al., "Assessment of Dysphagia with the Use of Pulse Oximetry", Dysphagia 14:152-156; Copyright Springer-Verlag New York Inc. 1999.

Tsien, Christine L., "TrendFinder: Automated Detection of Alarmable Trends", Massachusetts Institute of Technology, Jun. 2000 (241 pages).

ISR, PCT/US2007/020378, date of mailing Jul. 7, 2008.

* cited by examiner

SYSTEM AND METHOD FOR INTEGRATING VOICE WITH A MEDICAL DEVICE

CROSS-REFERENCES TO RELATED APPLICATION

This application is a continuation of U.S. patent application Ser. No. 11/540,457 filed on Sep. 29, 2006.

BACKGROUND OF THE INVENTION

1. Field of the Invention

The present invention relates generally to medical devices and, more particularly, to integrating voice controls and/or voice alerts into the medical device.

2. Description of the Related Art

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

In the field of medicine, doctors often desire to monitor certain physiological characteristics of their patients. Accordingly, a wide variety of devices have been developed for monitoring physiological characteristics. Such devices provide cargivers, such as doctors, nurses, and/or other healthcare personnel, with the information they need to provide the best possible healthcare for their patients. As a result, such monitoring devices have become an indispensable part of modern medicine.

For example, one technique for monitoring certain physiological characteristics of a patient is commonly referred to as pulse oximetry, and the devices built based upon pulse oximetry techniques are commonly referred to as pulse oximeters. Pulse oximetry may be used to measure various blood flow characteristics, such as the blood-oxygen saturation of hemoglobin in arterial blood, the volume of individual blood pulsations supplying the tissue, and/or the rate of blood pulsations corresponding to each heartbeat of a patient.

Pulse oximeters and other medical devices are typically mounted on stands that are positioned around a patient's bed or around an operating room table. When a caregiver desires to command the medical device (e.g., program, configure, and so-forth) they manipulate controls or push buttons on the monitoring device itself. The medical device typically provides results or responses to commands on a liquid crystal display ("LCD") screen mounted in an externally visible position within the monitoring device.

This conventional configuration, however, has several disadvantages. First, as described above, this conventional configuration relies upon physical contact with the monitoring device to input commands (e.g., pushing a button, turning a knob, and the like). Such physical contact, however, raises several concerns. Among these concerns are that in making contact with the medical device, the caregiver may spread illness or disease from room to room. More specifically, a caregiver may accidentally deposit germs (e.g., bacteria, viruses, and so forth) on the medical device while manipulating the device's controls. These germs may then be spread to the patient when a subsequent caregiver touches the medical device and then touches the patient. Moreover, if the medical device is moved from one patient room to another, germs transferred to the medical device via touch may be carried from one patient room to another. Even in operating rooms where medical devices are typically static, germs may be transferred onto a medical device during one surgery and subsequently transferred off the medical device during a later performed surgery.

Second, beyond contamination, monitoring devices that rely on physical contact for command input may clutter the caregiver's workspace. For example, because the medical device must be within an arm's length of the caregiver, the medical device may crowd the caregiver—potentially even restricting free movement of the caregiver. In addition, caregivers may have difficulty manipulating controls with gloved hands. For example, it may be difficult to grasp a knob or press a small button due to the added encumbrance of a latex glove.

Third, current trends in general medical device design focus on miniaturizing overall medical device size. However, as controls which rely on physical contact must be large enough for most, if not all, caregivers to manipulate with their hands, medical devices that employ these types of controls are limited in their possible miniaturization. For example, even if it were possible to produce a conventional oximeter that was the size of a postage stamp, it would be difficult to control this theoretical postage stamp-sized pulse oximeter with currently available techniques.

In addition, conventional techniques for outputting medical data also have several potential drawbacks. For example, as described above, conventional techniques for displaying outputs rely on LCD screens mounted on the medical device itself. Besides constantly consuming power, these LCD screens must be large enough to be visually accessed by a doctor or nurse. As such, the conventional LCD screens employed in typical medical devices also may be a barrier towards miniaturization of the medical device. Further, conventional screen-based output techniques may be impersonal to the patient and may lack configurability by the caregiver.

For at least the reasons set forth above, an improved system or method for interacting with a medical monitoring device would be desirable.

BRIEF DESCRIPTION OF THE DRAWINGS

Advantages of the invention may become apparent upon reading the following detailed description and upon reference to the drawings in which.

DETAILED DESCRIPTION OF SPECIFIC EMBODIMENTS

One or more specific embodiments of the present invention will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Figure 1:
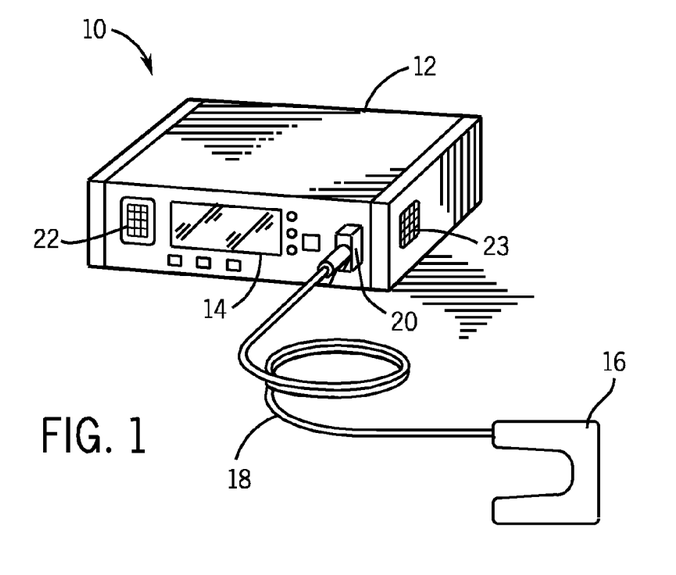
FIG. 1 is a diagrammatical representation of a pulse oximeter featuring an integral microphone in accordance with one embodiment of the present invention.

Turning initially to FIG. 1, an exemplary pulse oximeter featuring an integral microphone in accordance with one embodiment is illustrated and generally designated by the reference numeral 10. The pulse oximeter 10 may include a main unit 12 that houses hardware and/or software configured to calculate various physiological parameters. As illustrated, the main unit 12 may include a display 14 for displaying the calculated physiological parameters, such as oxygen saturation or pulse rate, to a caregiver or patient. In alternate embodiments, as described in further detail below, the display 14 may be omitted from the main unit 12.

The pulse oximeter 10 may also include a sensor 16 that may be connected to a body part (e.g., finger, forehead, toe, or earlobe) of a patient or a user. The sensor 16 may be configured to emit signals or waves into the patient's or user's tissue and detect these signals or waves after dispersion and/or reflection by the tissue. For example, the sensor 16 may be configured to emit light from two or more light emitting diodes ("LEDs") into pulsatile tissue (e.g., finger, forehead, toe, or earlobe) and then detect the transmitted light with a light detector (e.g., a photodiode or photo-detector) after the light has passed through the pulsatile tissue.

As those of ordinary skill in the art will appreciate, the amount of transmitted light that passes through the tissue generally varies in accordance with a changing amount of blood constituent in the tissue and the related light absorption. On a beat-by-beat basis, the heart pumps an incremental amount of arterial blood into the pulsatile tissue, which then drains back through the venous system. The amount of light that passes through the blood-perfused tissue varies with the cardiac-induced cycling arterial blood volume. For example, when the cardiac cycle causes more light-absorbing blood to be present in the tissue, less light travels through the tissue to strike the sensor's photo-detector. These pulsatile signals allow the pulse oximeter 10 to measure signal continuation caused by the tissue's arterial blood, because light absorption from other tissues remains generally unchanged in the relevant time span.

In alternate embodiments, the sensor 16 may take other suitable forms beside the form illustrated in FIG. 1. For example, the sensor 16 may be configured to be clipped onto a finger or earlobe or may be configured to be secured with tape or another static mounting technique. The sensor 16 may be connected to the main unit 12 via a cable 18 and a connector 20.

The pulse oximeter 10 may also include an integral microphone 22. As will be described further below, the integral microphone 22 may be configured to receive voice commands from a caregiver or user that can be processed into commands for the pulse oximeter 10. Although FIG. 1 illustrates the integral microphone 22 as being located on a front façade of the main unit 12, it will be appreciated that in alternate embodiments, the integral microphone 22 may be located at another suitable location on or within the main unit 12.

The pulse oximeter 10 may also include a speaker 23. As will be described further below, the speaker 23 may be configured to broadcast voice alerts or other suitable types of alerts to a caregiver or user. Although FIG. 1 illustrates the speaker 23 as being located on a side façade of the main unit 12, it will be appreciated that in alternate embodiments, the speaker 23 may be located at another suitable location on or within the main unit 12.

Figure 2:
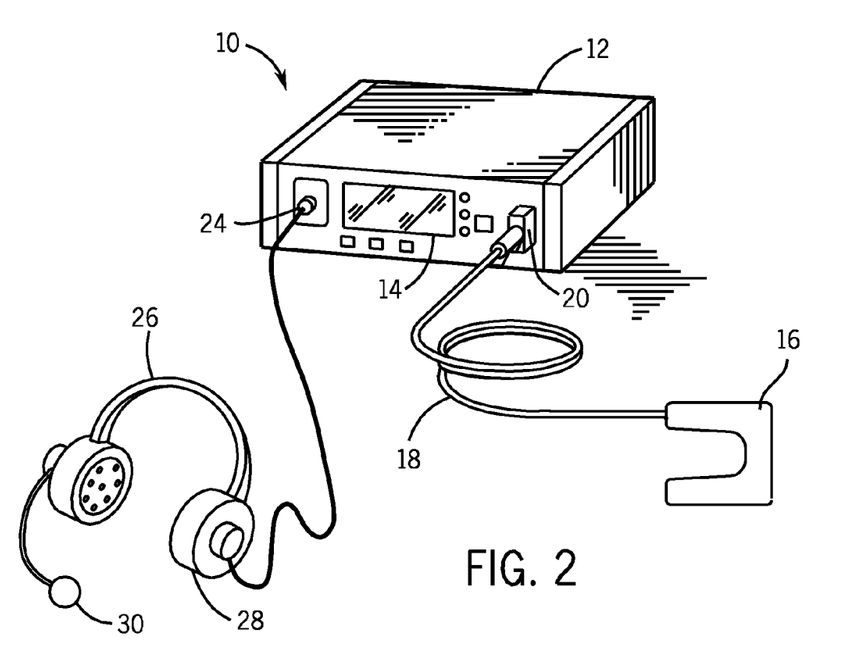
FIG. 2 is a diagrammatical representation of a pulse oximeter featuring an external microphone in accordance with one embodiment of the present invention.

Turning next to FIG. 2, another embodiment of the exemplary pulse oximeter 10 featuring an external microphone and speaker in accordance with one embodiment is illustrated. For simplicity, like reference numerals have been used to designate those features previously described in regard to FIG. 1. As illustrated, the pulse oximeter 10 of FIG. 2 also includes the main unit 12, the screen 14, the sensor 16, the cable 18, and the connector 20. However, in place of or in addition to the integral microphone 22, the pulse oximeter 10 illustrated in FIG. 2 may also include an audio connector 24 suitable for coupling a headset 26 to the main unit 12.

As illustrated in FIG. 2, the headset 26 may include one or more speakers 28 and an external microphone 30. As will be described further below, the one or more external speakers 28 may be employed by the pulse oximeter 10 to broadcast voice alerts or other suitable alerts to a caregiver or user. In addition, the external microphone 30 may be employed to receive voice commands for the pulse oximeter 10, as described further below.

Figure 3:
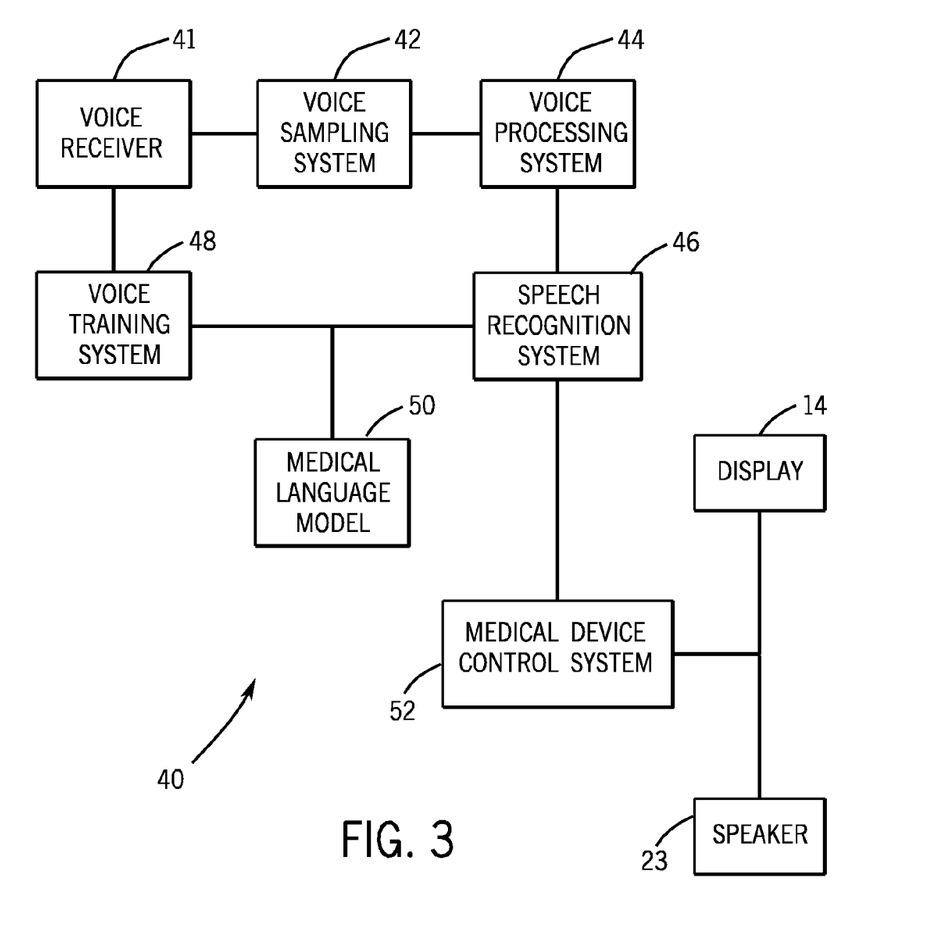
FIG. 3 is a block diagram of a medical device configured for voice control in accordance with one embodiment of the present invention.

FIG. 3 is a block diagram of an exemplary medical device 40 configured for voice control in accordance with one embodiment. For simplicity, like reference numerals have been used to designate those features previously described with regard to FIGS. 1 and 2. In one embodiment, the pulse oximeter 10 set forth in FIGS. 1 and/or 2 may comprise the medical device 40. As illustrated in FIG. 3, the medical device 40 may include a plurality of modules (blocks 41-52). These modules may be hardware, software, or some combination of hardware and software. Additionally, it will be appreciated that the modules shown in FIG. 3 are merely one exemplary embodiment and other embodiments can be envisaged wherein the module functions are split up differently or wherein some modules are not included or other modules are included.

As illustrated in FIG. 3, the medical device 40 may include a voice receiver 41. The voice receiver 41 may include any suitable form of microphone or voice recording device, such as the integral microphone 22 (as illustrated in FIG. 1) or the external microphone 30 (as illustrated in FIG. 2). As those of ordinary skill in the art will appreciate, the voice receiver 41 may be configured to receive a voice (i.e., an acoustic wave) and to convert the voice into an electronic analog waveform.

The voice receiver 41 may be configured to transmit the analog waveform to a voice sampling system 42. The voice sampling system 42 may be configured to sample the analog waveform to create digital voice data. For example, in one embodiment, the voice sampling system 42 may be configured to sample the electronic analog waveform 16,000 times per second to create a digital waveform of pulse amplitudes. In alternate embodiments, other suitable sampling techniques may be employed.

The voice processing system 44 may be configured to receive the digital waveform from the voice sampling system 42 and to convert the digital waveform into frequencies that can be recognized by a speech recognition system 46. In one embodiment, the voice processing system 44 may be configured to perform a fast fourier transform on the incoming digital waveform to generate a plurality of frequencies. The voice processing system 44 may then transmit the plurality of frequencies to the speech recognition system 46.

The speech recognition system 46 may be pre-populated or programmed with a plurality of frequency combinations that are associated with commands for the medical device 40. For example, frequencies combinations associated with the voice command "turn off alarm" may be associated with a command for the medical device 40 to silence an alarm. As mentioned above, in one embodiment, the particular frequency combinations may be pre-programmed or pre-configured. However, in alternate embodiments, the frequency combinations may be programmed into the speech database via a voice training system 48, which will be described in greater detail below.

In addition, the speech recognition system 46 may also be coupled to a medical language model 50. The medical language model 50 may be programmed with a plurality of command combinations that are prevalently used in controlling the medical device 40. For example, if the medical device 40 were an oximeter, such as the pulse oximeter 10, the medical language model 50 may store command combinations such as "turn oximeter off," "turn alarm off," "adjust volume," "pause alarms," and so-forth. In this way, the medical language model 50 may assist the speech recognition system 46 in determining the medical command associated with a particular voice command.

More specifically, in one embodiment, the medical language model 50 may assist the speech recognition system 46 in determining the proper medical command when the speech recognition system 46 is able to recognize some portion but not all of a voice command. For example, if the speech recognition system 46 is able to recognize the first and third words of the medical command "turn off alarms," but is unable to recognize the second word, the speech recognition system 46 may search the medical language model 50 for command combinations matching the recognized terms (i.e., "turn" and "alarms"). Because the medical language model 50 may be programmed with only those commands relevant to the operation of the medical device 40, the medical language model 50 enables the successful recognition of medical commands that would otherwise be unrecognizable by conventional, generic voice recognition systems. The medical language model 50 may be preprogrammed, may be programmed through the voice training system 48, or may be programmed via an external computer (not shown).

Upon recognizing a voice command as a command for the medical device 40, the speech recognition system 44 may be configured to transmit the command to a pulse medical device system 52. As will be appreciated by those with ordinary skill in the art, the medical device control system 52 may be configured to control the medical device. For example, if the medical device 40 were the pulse oximeter 10, the control system 52 would be configured to control the main unit 12 as well as the sensor 16 to produce physiological monitoring results and/or alarms, which may be transmitted to the display 14 or the speaker 23.

Figure 4:
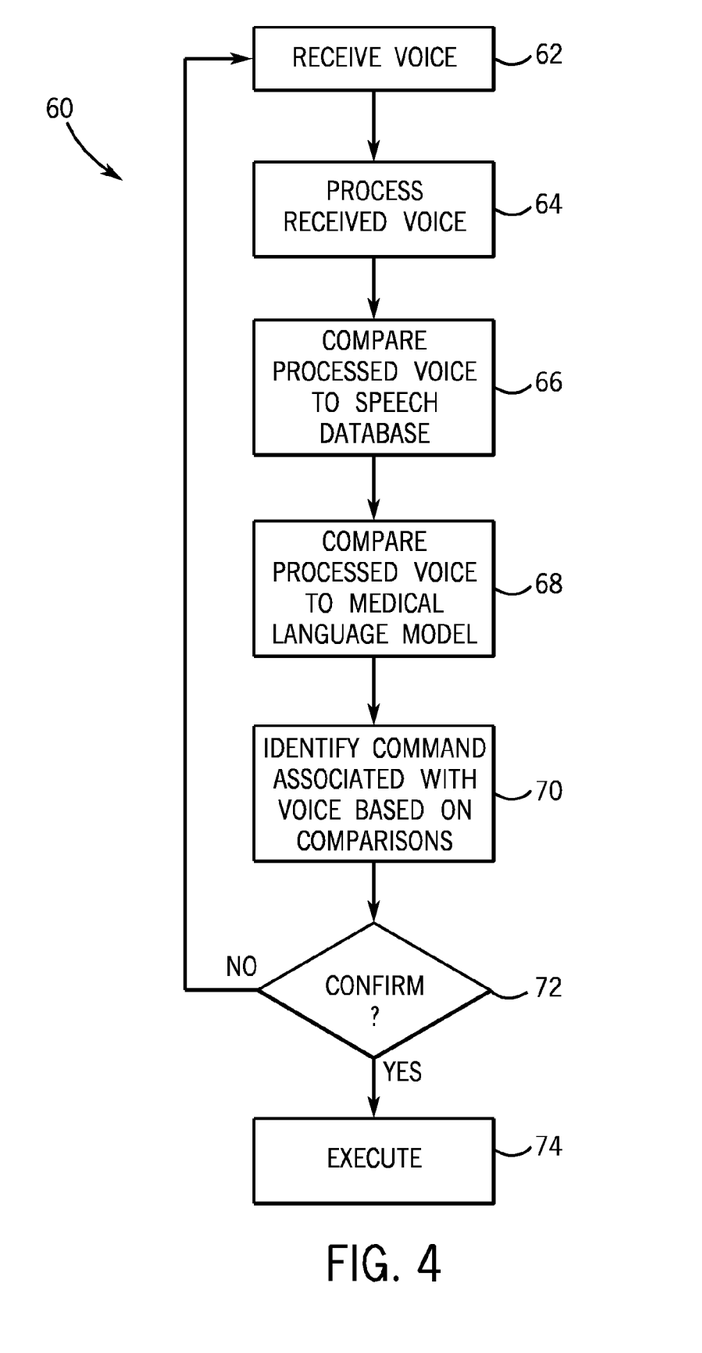
FIG. 4 is a flow chart illustrating an exemplary technique for processing a voice command in accordance with one embodiment of the present invention.

Turning next to FIG. 4, a flow chart illustrating an exemplary technique for processing a voice command in accordance with one embodiment is illustrated and generally designated by a reference numeral 60. In one embodiment, the technique 60 may be employed by the medical device 40 (as illustrated in FIG. 3) or the pulse oximeter 10 (as illustrated in FIGS. 1 and 2). It will be appreciated, however, that the technique 60 may also be employed by any other suitable type of medical device including, but not limited to, other forms of monitors, respirators, or scanners.

As illustrated by block 62 of FIG. 4, the technique 60 may begin by receiving a voice (i.e., a portion of spoken audio). For example, in one embodiment, the pulse oximeter 10 may receive the voice via the microphone 23 or the microphone 30. After receiving the voice, the technique 60 may include processing the received voice, as indicated in block 64. In one embodiment, processing the received voice may include converting the received voice into one or more frequencies that can be recognized by a speech recognition system, such as the speech recognition system 46 illustrated in FIG. 3.

The technique 60 may also include comparing the processed voice with a speech database and/or a medical language model, as indicated by blocks 66 and 68, and as described above with regard to FIG. 3. For example, in one embodiment, blocks 66 and 68 may include comparing the processed voice to a speech database within the speech recognition system 46 and/or the medical language model 50.

After performing one or more of these comparisons, the technique 60 may involve identifying a medical device command associated with the processed voice based upon the one or more of the comparisons, as indicated by block 70. For example, if comparisons to the speech database and/or the medical language model indicate that the processed voice is a command to "turn off alarms," then technique 60 may involve identifying the medical device command as a command to turn off the medical device's alarms.

Next, after identifying the medical device command, the technique 60 may include prompting a user (e.g., the caregiver) to confirm the new patient information was correctly determined, as indicated by block 72. For example, in one embodiment, the pulse oximeter 10 may display the identified command on the display 14 and prompt the user to confirm the correctness of the identified command. If the user does not confirm the command (block 72), the technique 60 may cycle back to block 62 (see above) and re-prompt the user for the new patient information. If, however, the user confirms the command, the technique may execute the command, as indicated by block 74. For example, in one embodiment, the user may confirm the command by speaking the word "yes" or the word "execute" in response to the displayed command.

Figure 5A:
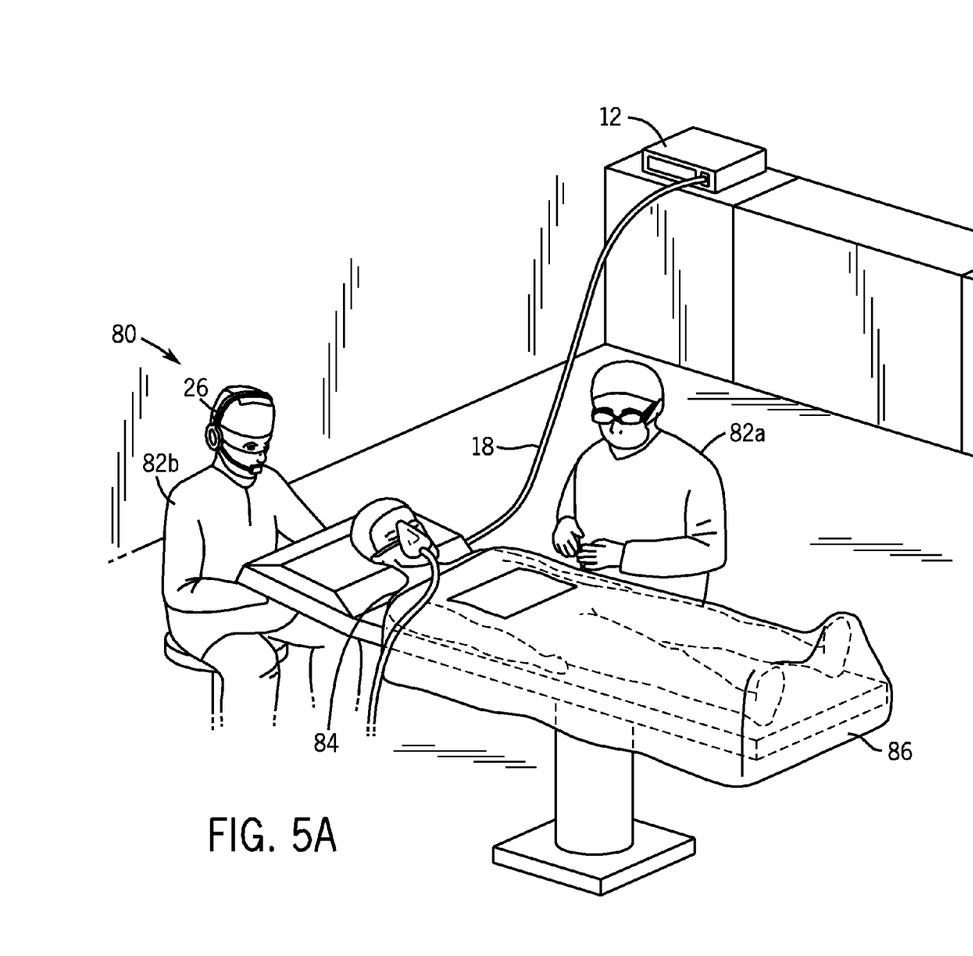
FIG. 5A illustrates an exemplary operating room employing a medical device configured for voice control in accordance with one embodiment of the present invention.

As described above, the pulse oximeter 10 and/or the medical device 40 may be employed in a variety of suitable medical procedures and/or environments. For example, FIG. 5A illustrates an exemplary operating room setting 80 employing the pulse oximeter 10 in accordance with one embodiment. As illustrated in FIG. 5A, the operating room 80 may include a first caregiver 82a, a second caregiver 82b, and a patient 84. In addition, the operating room 80 may also include an operating table 86 and the pulse oximeter 10.

Figure 5B:
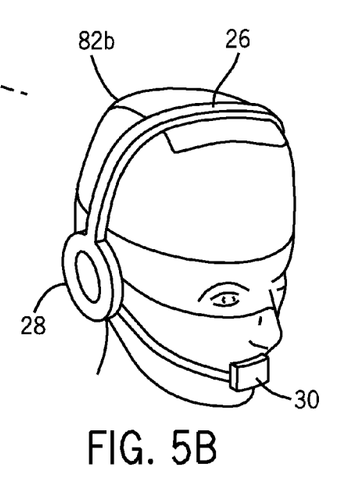
FIG. 5B illustrates an enlarged view of a caregiver employing a medical device configured for voice control in accordance with one embodiment of the present invention.

As illustrated, the caregiver 82*b* may employ and/or interact with the pulse oximeter 10 by wearing the headset 26. As highlighted in FIG. 5B, which illustrates an enlarged view of the caregiver 82*b*, the caregiver 82*b* may place the speaker 28 over his or her ear and place the external microphone 30 over his or her mouth. In this way, the caregiver 82*b* may receive alerts and issue commands from and to the main unit 12 via the headset 26. Advantageously, the functionality enables the main unit 12 to be placed at a remote location in the operating room 80 such that the main unit 12 does not crowd the medical procedure taking place in the operating room 80. However, those with ordinary skill in the art will appreciate that the embodiment set forth in FIGS. 5A and 5B is merely exemplary, and, as such, not intended to be exclusive. Accordingly, in alternate embodiments, the pulse oximeter 10 and/or the medical device 40 may be employed in any one of a number of suitable medical environments.

Figures 6, 7:
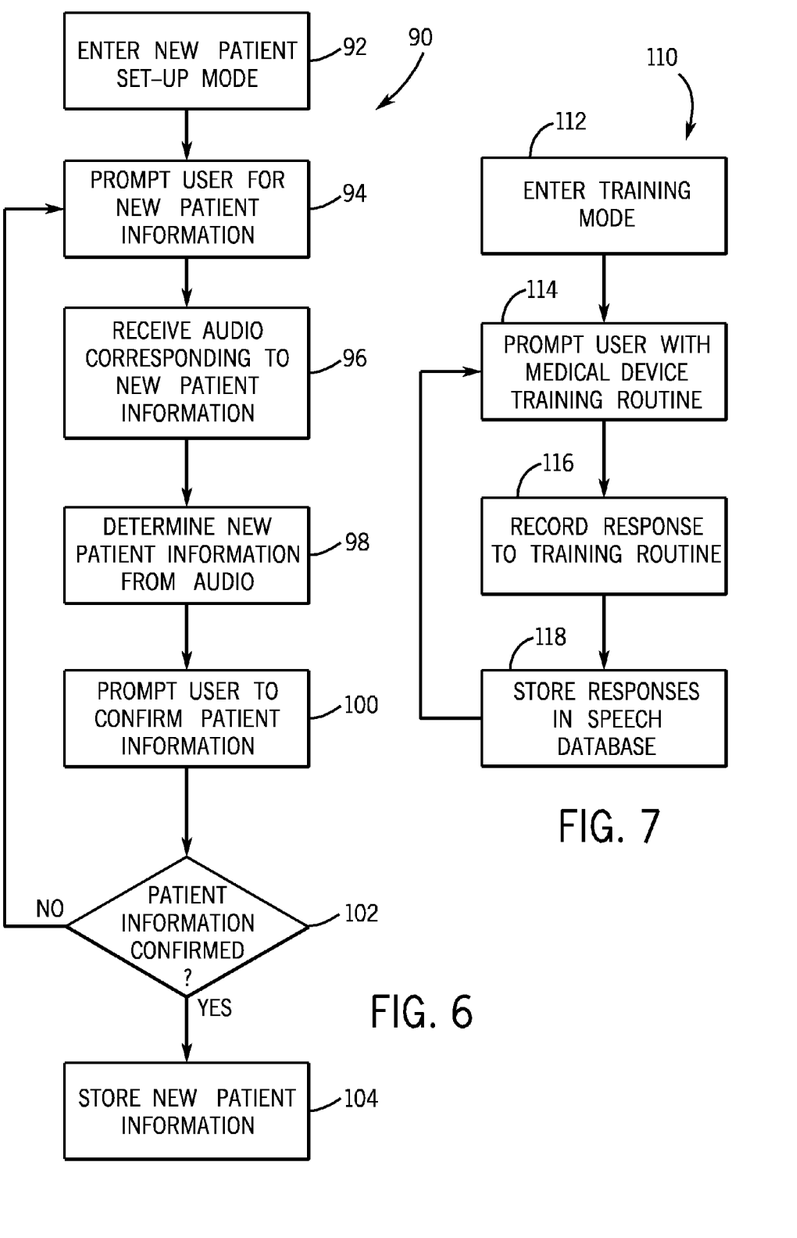
FIG. 6 is a flow chart illustrating an exemplary technique for setting up a patient record in a medical device in accordance with one embodiment of the present invention.
FIG. 7 is a flow chart illustrating an exemplary technique for training a voice system in a medical device in accordance with one embodiment of the present invention.

As described above, the pulse oximeter 10 and/or the medical device 40 may be configured to receive voice commands. Additionally, however, the pulse oximeter 10 and/or the medical device 40 may also be configured to enable entry of patient information by voice. For example, FIG. 6 is a flow chart illustrating an exemplary technique 90 for setting up a patient record in a medical device in accordance with one embodiment. In one embodiment, the technique 90 may be executed by the pulse oximeter 10 and/or the medical device 40.

As indicated by block 92 of FIG. 6, the technique 90 may begin by entering a new patent setup mode, as indicated by block 92. Next, the technique 90 may involve prompting a user for new patient information, as indicated by block 94. In one embodiment, prompting the user for new patient information may include displaying a message to the user on the display 14 (see FIGS. 1-3). Alternatively, prompting the user may involve an audio or voice prompt, as described further below, or another suitable form of user notification.

Next, the technique 90 may include receiving audio corresponding to the new patient information, as indicated by block 96. In one embodiment, audio corresponding to the new patient information may be received over the internal microphone 22 and/or the external microphone 30. For example, the external microphone 30 may receive patient information, such as patient name, age, and so-forth from the caregiver 82*b* wearing the headset 26. After receiving the audio corresponding to the new patient information, the technique 90 may involve determining the new patient information from the received audio, as indicated by block 98. In one embodiment, determining the new patient information may include processing the received audio and comparing the received audio to a speech database and/or medical language model, as described above with regard to FIGS. 3 and 4.

After determining the new patient information from the received audio, the technique 90 may include prompting a user (e.g., the caregiver 82*b*) to confirm the new patient information was correctly determined, as indicated by block 100. For example, in one embodiment, the pulse oximeter 10 may display the determined patient information on the display 14 and prompt the user to confirm the correctness of the determined patient information with a voice command (e.g., "correct," "yes," and so-forth). If the user does not confirm the new patient information (block 102), the technique 90 may cycle back to block 94 (see above) and re-prompt the user for the new patient information.

Alternatively, if the user does confirm the determined new patient information, the technique 90 may include storing the new patient information, as indicated by block 104. For example, in one embodiment, storing the new patient information may include storing the patient's name, age, and so-forth in a memory located within the pulse oximeter 10 and/or the medical device 40.

As described above, one or more embodiments described herein is directed towards a medical device configured to receive voice commands. Accordingly, FIG. 7 illustrates a technique 110 that may be employed to train a voice system in a medical device in accordance with one embodiment. In one embodiment, the technique 110 may be employed by the pulse oximeter 10 and/or the medical device 40. More specifically, in one embodiment, the technique 110 may be executed by the voice training system 48 of FIG. 3. However, it will be appreciated, that in alternate embodiments, other suitable medical devices may employ the technique 110.

As illustrated by block 112 of FIG. 7, the technique 110 may begin by entering a training mode. In one embodiment, the medical device 40 may be configured to enter a training mode in response to a depressed button or a sequence of depressed buttons on the medical device 40. Alternatively, in other embodiments, the pulse oximeter 10 and/or the medical device 40 may be configured to enter the training mode in response to a voice command and/or other suitable form of command or instruction.

After entering the training mode, the technique 110 may include prompting a user with a medical device training routine, as indicated by block 114. The medical device training routine may involve displaying one or more medical device specific words, phrases, or commands on the display 14. For example, the pulse oximeter 10 may be configured to display commands such as "turn off alarms," "turn down volume," "show pleth," or any other suitable voice command or instruction.

After prompting the user, as described above, the technique 110 may include recording a response to the training routine, as indicated by block 116. For example, the pulse oximeter 10 and/or the medical device 40 may be configured to record the response to the training routine via the external microphone 30. After recording the response to the training routine, the technique 110 may include storing the response in a speech database, such as the speech database within the speech recognition system 46. After storing the response in the speech database, the technique 110 may cycle back to block 114 and repeat the training routine with additional words, phrases, or comments. In one embodiment, medical device 40 may be configured to cycle through blocks 114, 116, and 118 for each of a predefined group of words and instructions stored within the voice training system 48.

Figure 8:
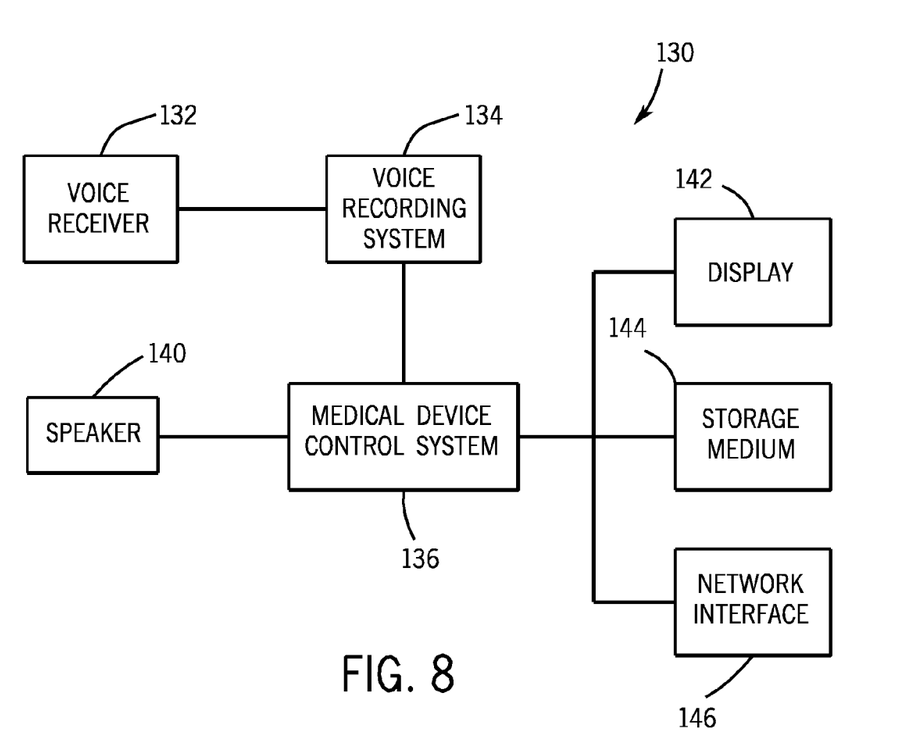
FIG. 8 is a block diagram of a medical device configured to broadcast voice alerts in accordance with one embodiment of the present invention.

Turning next to another embodiment, FIG. 8 is a block diagram of a medical device 130 configured to broadcast voice alerts in accordance with one embodiment. As those of ordinary skill in the art will appreciate, conventional medical devices are configured to use buzzes and/or beeps to indicate medical alerts or alarms (hereafter referred to collectively as "alerts"). In addition to disturbing patients and medical practitioners (and possibly breaking a medical professional's concentration), these buzzes and beeps typically provide no other useful information to a listener other than indicating the presence of an alert condition. Advantageously, the medical device 130 illustrated in FIG. 8 is configured to produce custom voice alerts that can advantageously provide detailed information about the alert conditions while at the same time being less jarring and/or abrasive than traditional medical device alerts.

The medical device 130 may include a voice receiver 132, such as the microphone 22 or the microphone 30 (FIGS. 1-2). As will be appreciated, the voice receiver 132 may be configured to receive audio patterns that may be employed to create voice alerts. The medical device 130 may also include a voice recording system 134 that may be configured to receive audio from the voice receiver 132 and to record the received audio.

The voice recording system 134 may be coupled to a medical device control system 136 that may be configured to receive the recorded audio and to store or play it, when appropriate, to produce voice alerts. For example, the medical device control system 136 may be configured to play an appropriate voice alert over a speaker 140. In addition, the medical device control system 136 may be coupled to a display 142. As will be appreciated, the display 142 may be configured to display instructions to a user during setup of the voice alerts as well as for other suitable user notifications.

Further, the medical device control system 136 may also be coupled to a storage medium 144. In one embodiment, the storage medium 144 is configured to store the recorded audio in an indexed format, such as a look-up table, link list, and so-forth, such that a portion of recorded audio may be associated with one or more alert conditions. As such, in this embodiment, the medical device control system 136, upon detecting an alert condition, may access the stored portion of recorded audio corresponding to the alert condition and then broadcast the portion of audio over the speaker 130.

As illustrated, the medical device 130 may also include a network interface 146. The network interface 146 may be configured to enable the medical device control system 136 to communicate with other computers or computerized devices over a network. In this capacity, the network interface 146 may allow the medical device control system 136 to download and/or upload portions of audio for use as voice alerts.

As described above, one or more of the embodiments set forth herein may be directed towards a medical device configured to produce voice alerts. Accordingly, FIG. 8 is a flow chart illustrating an exemplary technique 150 for setting up a voice alert in accordance with one embodiment. As such, in one embodiment, the technique 150 may be executed by the medical device 130.

Figure 9:
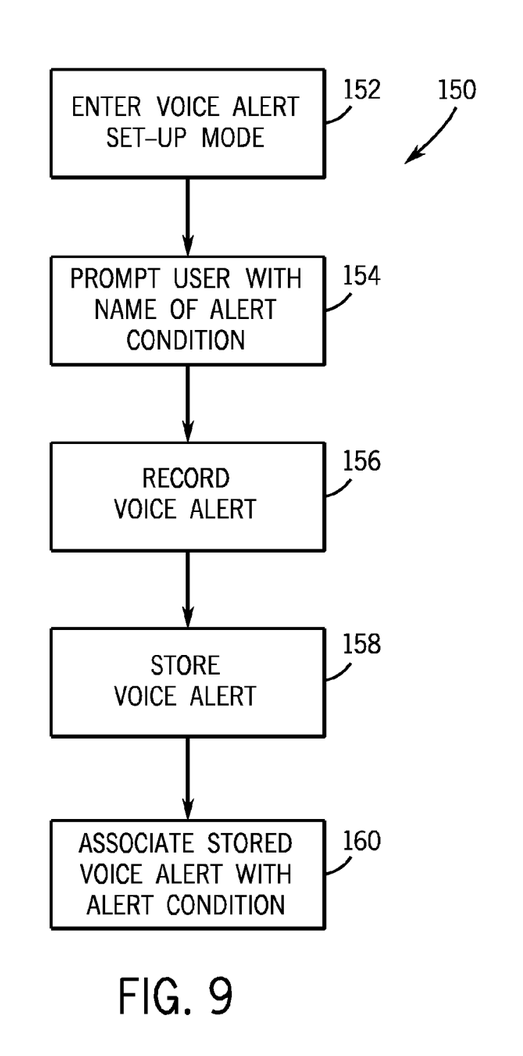
FIG. 9 is a flow chart illustrating an exemplary technique for setting up a voice alert in accordance with one embodiment of the present invention.

As illustrated by block 152 of FIG. 9, the technique 150 may begin by entering a voice alert setup mode. In various embodiments, entering a voice alert setup mode may be triggered by a voice command to the medical device 130, by physically manipulating one or more buttons on the medical device 130, or by another suitable technique. After entering the voice alert setup mode, the technique 150 may include prompting a user with a name of an alert condition. In one embodiment, the medical device 130 may prompt a user with a name of the alert condition by displaying the name of the alert condition on the display 142.

Next, the technique 150 may include recording a voice alert corresponding to the prompted alert condition. More specifically, in response to the prompt on the display 142, a user would speak the voice alert, which would subsequently be recorded as part of the technique 150. After recording the voice alert, technique 150 may include storing the voice alert (block 158) and associating the stored voice alert with the alert condition (block 160). For example, in one embodiment, the voice alert may be stored in the storage medium 144 and the medical device control system 136 may be configured to associate the stored voice alert with one or more of its alert conditions.

Figure 10:
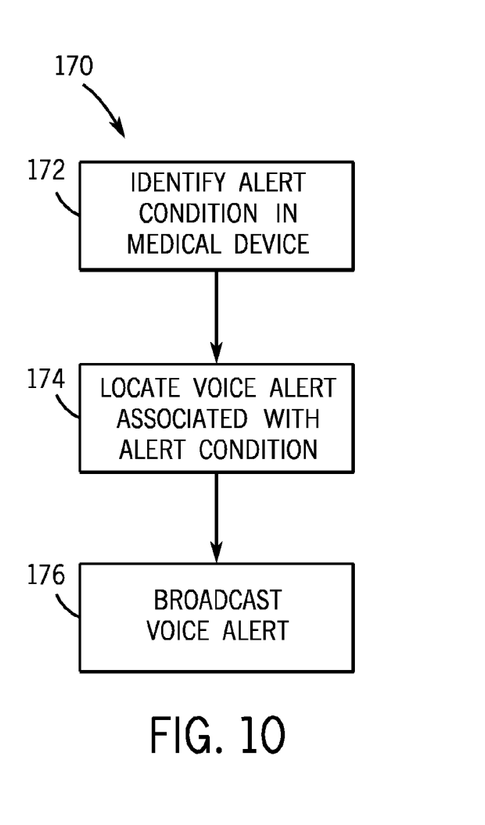
FIG. 10 is a block diagram illustrating an exemplary technique for broadcasting a voice alert in accordance with one embodiment of the present invention.

As described above, medical device 130 may be configured to broadcast voice alerts. Accordingly, FIG. 10 is a flow chart illustrating an exemplary technique 170 for broadcasting a voice alert in accordance with one embodiment. As shown, the technique 170 may begin by identifying an alert condition in the medical device 130. For example, in one embodiment, the medical device control system 136 may be configured to identify an alert condition, such as signal or power loss, as indicated by block 172.

Upon identifying the alert condition, the technique 170 may include locating a voice alert associated with the alert condition. For example, in one embodiment, the medical device control system 136 may locate a voice alert stored in the storage medium 144 that is associated with the alert condition. Lastly, the technique 170 may include broadcasting the voice alert, as indicated by block 176. For example, in one embodiment, the medical device control system 136 may be configured to broadcast the voice alert over the speaker 140.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims. Indeed, the present techniques may not only be applied to pulse oximeters, but also to other suitable medical devices. For example, the embodiments set forth herein may also be employed in respirators, ventilators, EEGs, medical cutting devices, and so-forth.

What is claimed is:

1. A pulse oximeter comprising:
a speech recognition system configured to:
receive a processed voice of a person proximate to the speech recognition system;
compare the processed voice to a speech database;
identify a command for the pulse oximeter corresponding to the processed voice based on the comparison; and
execute the identified pulse oximeter command without the person physically touching the pulse oximeter.

2. The pulse oximeter, as set forth in claim 1, comprising a tangible machine readable medium comprising a medical language model, wherein the speech recognition system is configured to identify the command based on the medical language model.

3. The pulse oximeter, as set forth in claim 2, wherein the medical language model comprises a plurality of commands for the pulse oximeter.

4. The pulse oximeter, as set forth in claim 1, comprising a voice training system configured to populate the speech database.

5. The pulse oximeter, as set forth in claim 1, comprising a voice processing system configured to process a received voice of the person proximate to the speech recognition system to create the processed voice.

6. The pulse oximeter, as set forth in claim 5, comprising a headset, wherein the voice processing system is configured to receive the received voice from the headset, wherein the headset is proximate to the pulse oximeter.

7. The pulse oximeter, as set forth in claim 5, comprising an integral microphone, wherein the voice processing system is configured to receive the voice of the person proximate to the speech recognition system from the integral microphone.

8. A method comprising:
receiving a processed voice of a person proximate to a pulse oximeter;
comparing the processed voice to a speech database disposed in the pulse oximeter;
identifying a command for the pulse oximeter corresponding to the processed voice based on the comparison; and
executing the identified pulse oximeter command without the person physically touching the pulse oximeter.

9. The method, as set forth in claim 8, comprising comparing the received processed voice to an oximeter language model.

10. A pulse oximeter comprising:
a control system configured to:
identify an alert condition for the pulse oximeter;
locate a voice alert corresponding to the alert condition; and
broadcast the voice alert over a speaker to a person proximate to the pulse oximeter.

11. The pulse oximeter, as set forth in claim 10, comprising a voice recording system configured to record the voice alert.

12. The pulse oximeter, as set forth in claim 11, comprising a storage medium, wherein the control system is configured to store the recorded voice alert on the storage medium.

13. The pulse oximeter, as set forth in claim 10, comprising a network interface, wherein the control system is configured to download the voice alert over the network interface.

14. A method of broadcasting voice alerts from a pulse oximeter, the method comprising:
prompting a user proximate to the pulse oximeter with a name of a pulse oximeter alert condition;
recording a voice alert of the user in the pulse oximeter;
associating the recorded voice alert with the pulse oximeter alert condition; and
broadcasting the recorded voice alert to a person proximate to the pulse oximeter when the alert condition is detected.

15. The method, as set forth in claim 14, comprising storing the voice alert in a memory disposed in the pulse oximeter.

16. A method for broadcasting a voice alert from a pulse oximeter, the method comprising:
identifying an alert condition for the pulse oximeter;
locating a voice alert corresponding to the alert condition; and
broadcasting the voice alert over a speaker integral to the pulse oximeter.

17. The method, as set forth in claim 16, wherein locating the voice alert comprises locating a recorded voice alert in a storage medium coupled to the pulse oximeter.

18. The method, as set forth in claim 16, wherein locating the voice alert comprises locating a recorded voice alert on a network via a network interface.

19. The method, as set forth in claim 16, wherein identifying the alert condition comprises identifying a loss of signal from a sensor placed on a patient proximate to the pulse oximeter.

20. A method for programming a pulse oximeter with patient information, the method comprising:
prompting a user proximate to the pulse oximeter for new patient information;
receiving audio corresponding to the new patient information using the pulse oximeter; and
determining the new patient information from the audio using the pulse oximeter.

21. The method, as set forth in claim 20, comprising:
prompting the user to confirm the determined new patient information; and
if the user confirms the new patient information, storing the new patient information in the pulse oximeter.

22. A medical device comprising:
one or more controls on the medical device, wherein activation of a respective control by physical touch executes a corresponding medical device command;
a speech recognition system configured to:
receive a processed voice of a person proximate to the speech recognition system;
compare the processed voice to a speech database;
identify a command for the medical device corresponding to the processed voice based on the comparison; and
execute the identified medical device command without the person physically touching the one or more controls.

23. The medical device, as set forth in claim 22, comprising a tangible machine readable medium comprising a medical language model, wherein the speech recognition system is configured to identify the command based on the medical language model.

24. The medical device, as set forth in claim 23, wherein the medical device comprises a pulse oximeter and the medical language model comprises a plurality of pulse oximeter commands.

25. The medical device, as set forth in claim 23, wherein the medical language model comprises a plurality of commands for the medical device.

26. The medical device, as set forth in claim 22, comprising a voice training system configured to populate the speech database.

* * * * *